United States Patent [19]

Dixon et al.

[11] Patent Number: 4,835,100

[45] Date of Patent: May 30, 1989

[54] METHOD AND TEST KIT FOR DETECTING AN AFLATOXIN $B_1$ AND $G_1$ USING NOVEL MONOCLONAL ANTIBODIES

[75] Inventors: Deborah E. Dixon; L. Patrick Hart, both of Lansing; James J. Pestka, East Lansing, all of Mich.

[73] Assignee: Neogen Corporation, Lansing, Mich.

[21] Appl. No.: 925,682

[22] Filed: Oct. 31, 1986

[51] Int. Cl.$^4$ ............... G01N 33/53; G01N 33/577; C12N 15/00; C12N 5/00

[52] U.S. Cl. ..................................... 435/7; 435/68; 435/172.2; 435/240.26; 435/240.27; 435/810; 436/518; 436/548; 436/808; 424/85.8; 530/387; 530/808; 530/809; 935/89; 935/90; 935/95; 935/103; 935/104; 935/106; 935/110

[58] Field of Search .................. 435/7, 810, 913, 915, 435/68, 172.2, 240.26, 240.27; 436/518, 548, 808, 815; 424/85; 530/387, 808, 809; 935/89, 90, 95, 103, 104, 106, 110

[56] References Cited

U.S. PATENT DOCUMENTS

4,281,061  7/1981  Zuk et al. .................. 436/537 X

OTHER PUBLICATIONS

Chu, F. S., Adv. Appl. Microbiol. 22, 83 (1971).
Gregory, J. F., et al., J. Assoc. Off. Anal. Chem, 65, 869 (1982).
Stubblefield, R. D., et al., J. Assoc. Anal. Chem. 60, 4066 (1977).
Chu, et al., Appl. Environ. Microbiol. 33, 1125 (1977).
El-Nakib, O., et al, J. Assoc, Off. Anal. Chem. 64, 1077 (1981).
Langone, J. L. et al., J. Natl. Cancer Inst. 56, 591 (1976).
Lawellin, D. W., et al., Appl. Environ, Microbiol. 34 94, (1977).
Pestka, et al., Appl Environ. Microbiol. 40, 1027 (1980).
Pestka et al., J. Fd. Prot. 47, 305 (1984).
Candlish, et al., J. E. Letter in Appl. Microbiol. 1, 57 (1985).
Groopman, et al., Proc. Natl. Acad. Sci. U.S.A. 81, 7728 (1984).
Haugen, et al., Proc. Natl. Acad. Sci. U.S.A. 18, 4124 (1981).
Chu, et al., J. Assoc. Off Anal. Chem. 60, 791 (1977).
Kitagawa et al., Chem. Pharm. Bull. 29, 1130 (1981).
Pestka, et al., Appl. Environ. Microbiol. 44, 1159 (1982).
Siraganian et al., Methods in Enzymology, vol. 92, pp. 11–23 (1983).
Galfre, et al., Methods in Enzymology, vol. 73, pp. 1–40 (1981).
Littlefield, J. W., Science 914, 709 (1964).
Goding, J. W., Monoclonial Antibodies: Principles and Practice (1983).
Sugasawara, et al., J. Immunol. Methods, 79, 263 (1985).
Wallin et al., Cancer Letters, 22, 163–170 (1984).
Eshhar et al., Steroids 38, 89–109 (1979).
Fantl, J. Steroid Biochem. 11, 125–130 (1982).
Kohen, F., et al., Steroids, 39, 453–459 (1982).
Gendloff et al., Phytopathology (1980).
Hunter et al., Appl. Environ. Microbiol. 49, 168–172 (1983).
Wouchik, et al., Appl. Environ. Microbiol. 48, 1096–1099 (1984).
Liu et al., Appl. Environ. Microbiol. 50, 332–336 (1985).
Warner, et al., J. Agr. Food Chem. 34: 714 (1986).

*Primary Examiner*—Robert J. Warden
*Assistant Examiner*—Jack Spiegel
*Attorney, Agent, or Firm*—Ian C. McLeod

[57] ABSTRACT

Novel monoclonal antibodies to an aflatoxin $B_1$ and $G_1$ in a test kit and used in a method of testing are described. The method for producing the monoclonal antibodies uses repeated administration of aflatoxin $B_1$ or the related analog compound as a 1-position polypeptide to a murine and production of a hybridoma to generate the novel monoclonal antibodies. The novel antibodies have limited cross-reactivity to aflatoxins $B_2$, $G_2$ and $M_1$. Aflatoxin $B_1$ or aflatoxin $G_1$ are detected in foods and the like using the test kit and method.

7 Claims, 2 Drawing Sheets

AFLATOXIN B1 CONCENTRATION (PPB)
INDIRECT ENZYME IMMUNO ASSAY
2F5 MONOCLONAL ANTIBODY

AFLATOXIN B1 CONCENTRATION (PPB)
DIRECT ENZYME IMMUNO ASSAY
2F5 MONOCLONAL ANTIBODY

METHOD AND TEST KIT FOR DETECTING AN AFLATOXIN $B_1$ AND $G_1$ USING NOVEL MONOCLONAL ANTIBODIES

BACKGROUND OF THE INVENTION (1) Field of the Invention

The present invention relates to novel monoclonal antibodies against aflatoxin $B_1$ and $G_1$ and to a test kit and a method which uses these monoclonal antibodies to detect the presence of aflatoxin $B_1$ and $G_1$ in foods and other materials. In particular the present invention relates to monoclonal antibodies produced (1) by repeated introduction of aflatoxin $B_1$ as a 1-position polypeptide conjugate into a murine over a period of time so that polyclonal antibodies are released into the blood serum of the murine and then (2) by the production of hybridomas from spleen cells of the murine which generate the monoclonal antibodies and which have substantially the cross-reactivity of the specific monoclonal antibody produced by hybridoma IVI-10108 to aflatoxin $B_1$ and $G_1$ and limited cross-reactivity to aflatoxins $B_2$, $G_2$ and $M_1$.

(2) Prior Art

Aflatoxins are toxic metabolites produced by the fungal species *Aspergillus flavus* and *Aspergillus parasiticus*. The ability of aflatoxin $B_1$ and its metabolites to act as potent carcinogens, mutagens and teratogens has been described (Butler, W. H. *Mycotoxins* p. 1–28 (1974); Chu, F. S., Adv. Appl. Microbiol. 22, 83 (1971)). Interest in development of rapid sensitive assays for detection of aflatoxins has been steadily increasing, since the compounds are known to occur naturally in peanuts, corn, milk, wheat, and animal rations (Butler, W. H. *Mycotoxins* p. 1–28 (1974)). Use of high performance liquid chromatography has been described for quantitation of aflatoxins (Gregory, J. F. and Manley, D. B., J. Assoc. Off. Anal. Chem. 65, 869 (1982); Stubblefield, R. D. and Shotwell, O. L., J. Assoc. Anal. Chem. 60. 4066 (1977)). Several drawbacks to using this procedure as a quick screening method include the high cost of the instrumentation, the need for extensive sample clean up, and only single samples may be analyzed at one time.

A number of immunoassays using polyclonal antiserum have been described for detection of aflatoxin $B_1$ (Chu, F. S. and Ueno, I. Appl. Environ. Microbiol. 33, 1125 (1977); El-Nakib, O., Pestka, J. J. and Chu, F. S., J. Assoc. Off. Anal. Chem. 64, 1077 (1981); Langone, J. L. and Van Vunakis, H., J. Natl. Cancer Inst. 56, 591 (1976); Lawellin, D. W., Grant, D. W. and Joyce, B. K., Appl. Environ. Microbiol. 34, 94 (1977); Pestka, J. J., Gaur, P. K. and Chu, F. S., Appl. Environ. Microbiol. 40, 1027 (1980); and Pestka, J. J. and Chu, F. S., J. Fd. Prot. 47, 305 (1984)). The advantages offered by these assays include a reduction in assay time, simplified extraction procedures, an increase in assay sensitivity, and the ability to routinely screen large numbers of samples.

In an attempt to compensate for the limitations encountered when using conventional polyclonal antisera assay systems (availability, potential antibody variation from bleeding to bleeding, and problems with large scale production of antibody), hybridoma cell lines, which secrete monoclonal antibodies to aflatoxin $B_1$ (or aflatoxin $B_1$-DNA adducts), have been produced (Candlish, A. A. G., Stimson, W. H. and Smith, J. E., Letters in Appl. Microbiol. 1, 57 (1985); Groopman, J. D., Haugen, A., Goodrich, G. R., Wogan, G. N. and Harris, C. C., Cancer Res. 42, 3120 (1982); Groopman, J. D., Trudel, L. J., Donahue, P. R., Marshak-Rothstein, A. and Wogan, G. N., Proc. Natl. Acad. Sci. U.S.A. 81, 7728 (1984); Haugen, A., Groopman, J. D., Hsu, I. C., Goodrich, G. R., Wogan, G. N. and Harris, C. C., Proc. Natl. Acad. Sci. U.S.A. 18, 4124 (1981)). The potential exists for the availability of an infinite supply of homogeneous antibody which can be mass produced. In a rapid assay (e.g. ten minutes) there is too little cross-reactivity with $G_1$ using these prior art monoclonal antibodies.

Thus monoclonal antibodies which recognize aflatoxin $B_1$, $B_2$ and $M_1$ are well known as shown by Candlish, A. A. G., Stimson, W. H. and Smith, J. E., Letters in Appl. Microbiol. 1, 57 (1985); Groopman, J. D., Trudel, L. J., Donahue, P. R., Marshak-Rothstein, A. and Wogan, G. N., Proc. Natl. Acad. Sci. USA 81, 7728 (1984). There is a need for monoclonal antibodies which react significantly with only $B_1$ and $G_1$. Aflatoxin $G_1$, is a major source of aflatoxin contamination in peanuts.

It would be advantageous to use monoclonal antibodies for conducting the immunoassays for aflatoxin $B_1$ and $G_1$. Hybridomas produce unlimited amounts of highly uniform monoclonal antibodies. The monoclonal antibodies can then be used in the development of a colorimetric commercial assay systems for the mycotoxins, such as Enzyme Linked Immunosorbent Assay (ELISA) or fluorescent antibody tests.

OBJECTS

It is therefore an object of the present invention to provide a highly specific and sensitive assay method and test kit for aflatoxin $B_1$ and $G_1$ using novel monoclonal antibodies. These and other objects will become increasingly apparent by reference to the following description and the drawings.

IN THE DRAWINGS

FIG. 1 is a graph showing the inhibitory effects of several concentrations of aflatoxin $B_1$ or various analogs. The concentration of aflatoxin $B_1$ or analogs of monoclonal antibody (2F5) binding in competitive indirect-ELISA were determined from the graph as follows: (X) aflatoxin $B_1$, 2.8 ng/ml; (+) aflatoxin $B_2$, 70.8 ng/ml; (*) aflatoxin $G_1$, 1.6 ng/ml; (▼) aflatoxin $G_2$, 56.2 ng/ml; and (O) aflatoxin $M_1$, 63.1 ng/ml.

GENERAL DESCRIPTION

Figure 2:
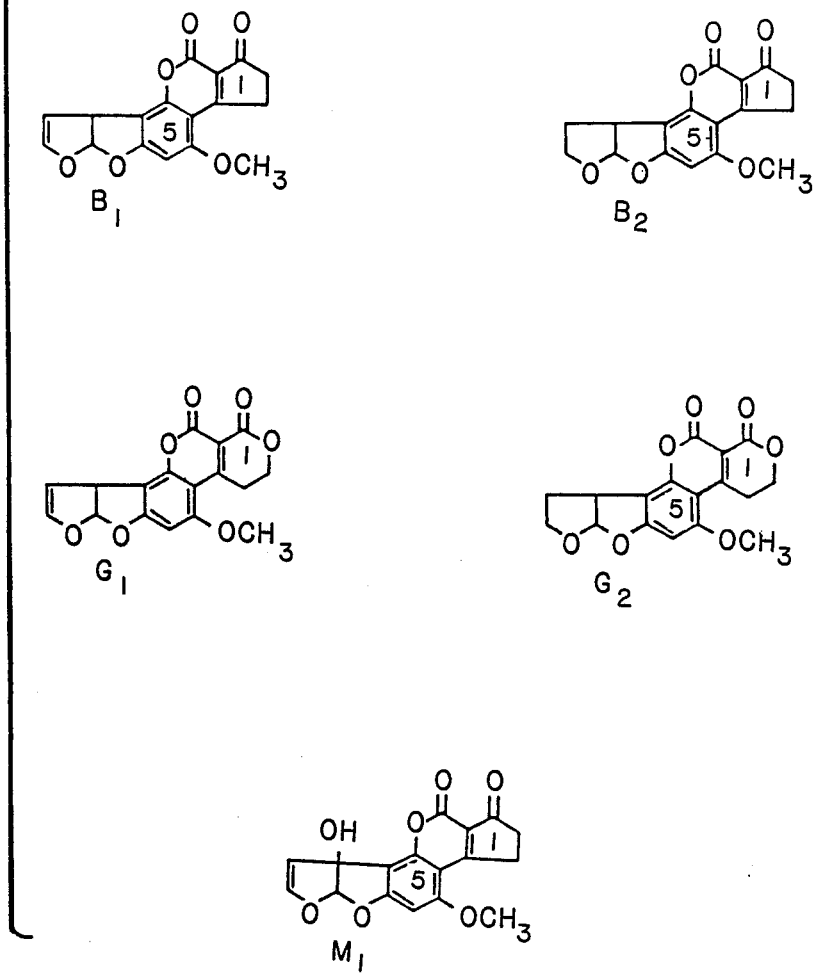
FIG. 2 shows structures of aflatoxin $B_1$ and metabolites tested for cross-reactivity.
Figure 4:
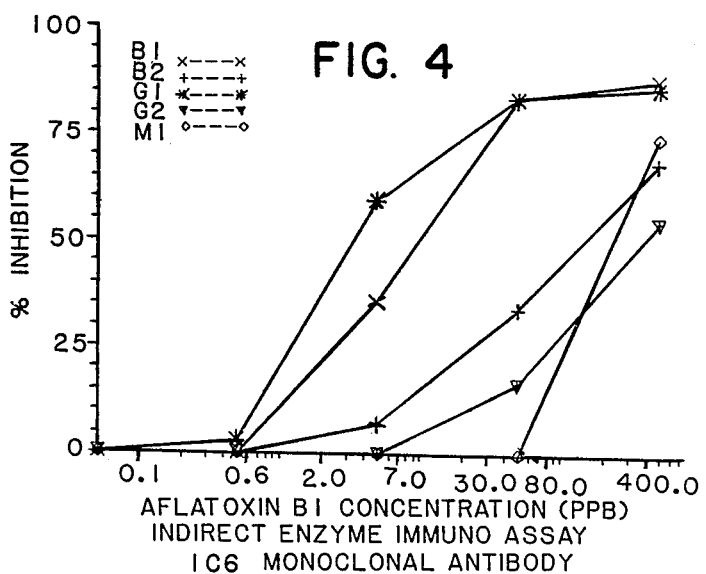
FIG. 4 is a graph showing the concentration of aflatoxin $B_1$ and analogs required to inhibit fifty percent (50%) of antibody binding in CI-ELISA with a different monoclonal antibody (1C6).

The present invention relates to an improvement in a test kit for detecting aflatoxin $B_1$ and related analog compounds as an antigen using an immunoassay wherein a label on an antigen or an antibody is detected to determine the unknown antigen, which comprises: providing in the test kit a monoclonal antibody to the aflatoxins $B_1$ and $G_1$, wherein the antibody is derived by repeatedly introducing aflatoxin $B_1$ or $G_1$ as a 1-position polypeptide conjugate into a murine so that polyclonal antibodies are provided in the blood serum of the murine, by forming a hybridoma with spleen cells from the murine and myeloma cells and by isolating the hybridoma which produces a monoclonal antibody which specifically binds the aflatoxins $B_1$ and $G_1$ and wherein the monoclonal antibody has a cross-reactivity to the related analog compounds of a specific monoclonal antibody derived from hybridoma IVI 10108 so that the monoclonal antibody reacts with aflatoxin $B_1$ and $G_1$ and has limited cross-reactivity with aflatoxins $B_2$, $G_2$ and $M_1$.

Further the present invention relates to a method for testing for an unknown amount of aflatoxin $B_1$ or related analog compound in an immunoassay wherein a labeled known antigen or antibody is used to determine an unknown antigen the improvement which comprises; providing a monoclonal antibody to the aflatoxins $B_1$ and $G_1$, wherein the monoclonal antibody is derived by repeatedly introducing aflatoxin $B_1$ or $G_1$ as a 1-position polypeptide conjugate into a murine so that polyclonal antibodies are provided in the blood serum of the murine, by forming a hybridoma with spleen cells from the murine and myeloma cells and by isolating the hybridoma which produces the monoclonal antibody which is specific for aflatoxins $B_1$ and $G_1$ and wherein the monoclonal antibody has a cross-reactivity to the related analog compounds of a specific antibody derived from hybridoma IVI 10108 so that the monoclonal antibody reacts with aflatoxin $B_1$ and $G_1$ and has limited cross-reactivity with aflatoxins $B_2$, $G_2$ and $M_1$; and testing for the unknown aflatoxin $B_1$ or $G_1$ using the monoclonal antibody.

Finally the present invention relates to novel monoclonal antibodies having the cross-reactivity with aflatoxin $B_1$ and $G_1$ of an antibody produced by the preferred hybridoma cell lines. In particular the present invention relates to hybridoma IVI-10108 (internal reference 2F5) and to related hybridomas produced with the preferred murine myeloma ATCC TIB 18 and murine spleen cells. The ATCC is the American Type Culture Collection, Rockville, Md. and the IVI is In Vitro International, Inc., 7885 Jackson Road, Ann Arbor, Mich. 48103. Monoclonal antibody 1C6 is deposited at Neogen Corporation and at Michigan State University of Lansing and East Lansing, Mich., respectively. The monoclonal antibodies are $IgG_1$ with kappa light chains.

The term "polypeptide" as used herein includes natural proteins as well as synthetically produced proteins which have varying molecular weights. Bovine serum albumin and ovalbumin are examples of proteins and poly L lysine is an example of a synthetically produced protein. The purpose of these proteins is to concentrate the aflatoxin $B_1$ on the surface of the polypeptide so that polyclonal antibodies are developed in the blood serum of the mice.

To produce the monoclonal antibodies, the mice are treated with the 1-position polypeptide aflatoxin $B_1$ or $G_1$ conjugate so as to provide polyclonal antibodies in the blood serum of the murine. Preferably the mice are injected subcutaneously at about two to four (2 to 4) week intervals with between 250 to 500 micrograms of an aflatoxin $B_1$ bovine serum albumin conjugate. Spleen cells from the mice are isolated and fused to the myeloma cells to produce a hybridoma using known procedures. The cells are then screened for specific monoclonal antibody production against aflatoxin $B_1$.

SPECIFIC DESCRIPTION

The following is a description of the preferred embodiment of the present invention.

Following immunization of BALB/c female mice with massive subcutaneous doses of aflatoxin $B_1$ conjugated to bovine serum albumin in the 1-position, the spleen cells from the mouse whose serum showed the best percentage of inhibition of antibody were fused with NS-1 myeloma cells. A stabilized cell line secreting monoclonal antibody of subclass $IgG_1$ with kappa light chains was obtained. A competitive indirect enzyme-linked immunosorbent assay (CI-ELISA) employing this antibody was used for detection of aflatoxin $B_1$ with a detection limit of 0.5 ng/ml. Cross-reactivity of the monoclonal antibody, as determined by relative concentrations (ng/ml) of aflatoxin $B_1$ metabolites for 50% inhibition of antibody binding in the ELISA, was as follows: aflatoxin $B_1$, 2.8 ng/ml; aflatoxin $B_2$, 70.8 ng/ml; aflatoxin $G_1$, 1.6 ng/ml; aflatoxin $G_2$, 56.2 ng/ml; and aflatoxin $M_1$, 63.1 ng/ml. A ten (10) minute competitive direct ELISA (CD-ELISA) has been developed with a detection limit for aflatoxin $B_1$ of 0.5 ng/ml.

EXPERIMENTAL

Materials: All inorganic chemicals and organic solvents were of reagent grade or better. Bovine serum albumin (BSA) (fatty acid free and fraction V) ovalbumin (OA) (crude and fraction VII), polyethylene sorbitan monolaurate (Tween 20), 2,2'-azino-di-(3-ethyl-bentzthiazoline)sulfonic acid (ABTS), hydrogen peroxide dicyclohexylcarbodiimide, N-hydroxysuccidimide, dimethylformamide (DMF), polyethylene glycol (PEG) (MW 1450), insulin, oxaloacetate, hypoxanthine (H), amino-pterin (A), thymidine (T) and 2,6,10,14 tetramethylpentadecane (pristane), horseradish peroxidase (HRP) Type VI were purchased from Sigma Chemical Company (St. Louis, Mo.); tetrahydrofuran from Aldrich Chemical Company (Milwaukee, Wis.); Freund's complete and incomplete adjuvants from Difco (Detroit, Mich.); goat anti-mouse IgG conjugated to horseradish peroxidase from Cooper Biomedical (Malvern, Pa.); Dulbecco's Modified Eagle's Medium (DMEM), Penicillin/Streptomycin Solution (Pen/Strep) (100,000 U/ml), NCTC Medium 135, fetal bovine serum (FBS), and sodium pyruvate from Gibco Laboratories (Grand Island, N.Y.); microculture plates (96- and 24-well plates) from Costar (Cambridge, Mass.); microtiter plates from NUNC, Vangard International (Neptune, N.J.). Aflatoxins $B_1$, $B_2$, $G_1$, $G_2$ were purchased from Sigma Chemical Company (St. Louis, Mo.); aflatoxin $M_1$ was generously provided by the Department of Botany and Plant Pathology, Michigan State University, East Lansing, Mich. Subclass identification kit was purchased from Boehringer Mannheim Biochemicals (Indianapolis, Ind.). The myeloma cell line P3/NS 1/1-Ag-4 (NS-1) (ATCC TIB 18) was purchased from The American Type Culture Collection (Rockville, Md.). Mice were purchased from Charles River Laboratories (Wilmington, Mass.).

Preparation of Conjugate Antigens: Aflatoxin $B_1$ was conjugated to BSA (aflatoxin $B_1$-BSA) for use as immunogen and to OA (aflatoxin $B_1$-OA) for use as a solid phase antigen in the competitive indirect ELISA (CI-ELISA). Since aflatoxin $B_1$ possesses no reactive groups for conjugation, it was first converted to aflatoxin-$B_1$-carboxymethylamine (aflatoxin $B_1$-oxime) in the 1-position by the method of Chu, Hsia and Sun (Chu, F. S., Hsia, M-T. S., and Sun. P., J. Assoc. Off. Anal. Chem. 60, 791 (1977)) and then conjugated to BSA or OA (fraction VII) by the N-hydroxysuccinimide procedure of Kitagawa et al (Kitagawa T., Shimozono, T., Aikawa, T., Yoshido, T. and Nishimura H., Chem. Pharm. Bull. 29, 1130 (1981)). The molar ratio of aflatoxin $B_1$ conjugated to protein was determined spectrophometrically, using an absorption maxima of 360 nm and an extinction coefficient of 21,800. For each mole of BSA and OA, 1 and 10 moles of aflatoxin $B_1$ were conjugated to the two proteins, respectively. Aflatoxin $B_1$-BSA was lyophilized and stored at $-80°$ C. and aflatoxin $B_1$-OA was stored in small aliquots (0.5 ml) at $-20°$ C.

Immunization Protocol: Three BALB/c female mice, eight to ten weeks of age, weighing approximately 18 g, were subcutaneously injected three times with aflatoxin $B_1$-BSA. The first three doses (0.5 mg/0.5 ml saline), given at two week intervals, were injected into a single site on the back. One week following the third injection, serum was collected from the retrobulbar plexus of each mouse and a titration of antibody in all the sera was performed using an indirect ELISA. CI-ELISA was also performed to determine which serum contained the most sensitive antibody. The spleen from the mouse with serum showing optimal relative inhibition was used for fusion. The third injection followed a seven (7) month resting period. Four days prior to fusion, the mouse was injected intraperitoneally with 250 ug of the conjugate antigen (0.25 ml in saline).

Titration of Antiserum by a Competitive Indirect ELISA: One hundred (100) ul of aflatoxin $B_1$-OA (10 ug/ml dissolved in 0.15M carbonate-bicarbonate buffer, pH 9.6) were added to each well of a 96-well microtiter plate and incubated overnight at 4° C. Unbound conjugate was removed from the plate with four washes (250 ul) of 0.1M phosphate buffered saline (PBS, pH 7.2) containing 0.20% Tween 20 (vol/vol) (PBS-Tween). Unbound solid phase sites were blocked by adding 300 ul of 1% (wt/vol) crude OA in PBS to each well and incubating, for 30 min at 37° C. The plate was washed four more times with PBS-Tween and duplicate aliquots of antiserum serially diluted in PBS (100 ul) were added to the wells and incubated for one hour at 37° C. Duplicate wells of serially diluted pre-immune serum were used as the control. Unbound antibody was removed by washing four times with PBS-Tween. To each well, 100 ul of goat anti-mouse IgG conjugated to horseradish peroxidase (diluted 1:500 in 1% OA-PBS) were added. Following incubation for 30 min at 37° C. the plate was washed eight times with PBS-Tween. Bound peroxidase was determined with ABTS substrate as described previously (Pestka, J. J., Li, Y. K. and Chu, F. S., Appl. Environ. Microbiol. 44, 1159 (1982)). Absorbance was read at 405 nm and the endpoint titer for each serum was arbitrarily designated as the maximum dilution which gave twice or greater the absorbance of the same dilution of non-immune control serum.

Competitive Indirect ELISA: CI-ELISA was used to (1) determine the sensitivity of anti-aflatoxin $B_1$ antibodies in mouse sera produced during the course of immunization, (2) to identify culture wells containing hybridomas secreting the desired antibody following fusion and cloning, and (3) determine the sensitivity and specificity of the monoclonal antibody secreted by the stabilized cell line. Briefly, microtiter plates were coated with solid phase aflatoxin $B_1$-OA and blocked with OA as described in the indirect titration procedure. Next 50 ul aliquots of aflatoxin $B_1$ (or metabolite) dissolved in 1% (vol/vol) methanol in PBS (1% MeOH-PBS) were simultaneously incubated with 50 ul antiserum (diluted 1:100 in PBS) or 50 ul crude supernatant over the aflatoxin $B_1$-OA solid phase for one hour at 37° C. Bound antibody was then determined by the addition of goat anti-mouse IgG peroxidase conjugate as described above.

To identify cultures containing anti-aflatoxin $B_1$ antibody in fusion wells and cloning wells, 50 ul aliquots of 1% MeOH-PBS were added as aflatoxin $B_1$ free blanks to each of two aflatoxin $B_1$-OA coated wells and 50 ul aliquots of aflatoxin $B_1$ (500 ng/ml diluted in 1% MeOH-PBS) were added to the two additional aflatoxin $B_1$-OA other coated wells. To each of these four wells, 50 ul aliquots of culture supernatant were added. Following a two hour incubation period at 37° C., wells were washed four times, and then incubated for one hour with goat anti-mouse IgG peroxidase conjugate. The assay was then completed as described above.

Competitive Direct ELISA (CD-ELISA): A one hour assay was developed using the monoclonal antibody. Briefly, 50 ul aliquots of purified ascites fluid (diluted 1:400 in carbonate-bicarbonate buffer, pH 9.6) were added to each well in a microtiter plate. The antibody was adsorbed onto the plastic solid phase when the plate was placed in a 40° C. drying oven for 6 hr. The plate was washed three times with PBS-Tween to remove any unbound antibody. A 1% solution (wt/vol) of bovine serum albumin diluted in PBS (1% BSA-PBS) (300 ul) was added to each well and incubated for 30 min at 37° C. The plate was washed three times. Aflatoxin $B_1$ standards (or metabolite) were mixed in equal volumes with aflatoxin $B_1$ conjugated to horseradish peroxidase (aflatoxin $B_1$-HRP conjugate) diluted 400 fold in blocking solution containing 1% (vol/vol) DMF. Fifty (50) ul aliquots of the mixture were added to the wells and the plate was incubated for 10 min at 37° C. The plate was washed five times and ABTS substrate (100 ul) was added and incubated for 15 min at 37° C. The assay was completed in the same manner as the competitive indirect assay.

Monoclonal Antibody Production: Spleen cells and myeloma cells (NS-1) were fused with PEG by the method of Siraganian et al (Siraganian, R. P., Fox, P. C. and Berenstein, E. H., Methods in Enzymology, Vol. 92, p. 17–23, (1983)). The fused cells were suspended in Dulbecco's Modified Eagle's Medium containing 20% (vol/vol) fetal bovine serum (20% FBS-DMEM) and supplemented with 1% NCTC, 5 mM oxaloacetate, 10 mM sodium pyruvate, and insulin (75.5 mg/L). Pen/Strep solution was added (100 $\mu$/ml) to minimize bacterial contamination. A feeder layer of spleen cells (final concentration of $1 \times 10^5$ cell/ml) was mixed with the fused cells (Galfre, G. and Milstein, C., Methods in Enzymology. Vol. 73, p. 1–40 (1981)) and the sixty innermost wells of (16) microculture plates were seeded with 0.2 ml of this mixture; the outer wells were filled with sterile medium. Plates were incubated at 37° C. in an atmosphere of 8% $CO_2$.

Twenty-four hours following fusion, half of the culture supernatant fraction from each well was removed by aspiration, and 0.1 ml of hypoxanthine-aminopterin-thymidine (HAT) medium was added (Littlefield, J. W., Science 914,709 (1964)). The HAT medium was changed every three days for a 14 day period. The cultures were then fed with hypoxanthine-thymidine (HT) medium until they were frozen and stored in liquid nitrogen. CI-ELISA screening of supernatants were performed over a one week period from day 14 to day 21 following fusion.

Cells in the fusion wells with supernatants showing at least 40% inibition in CI-ELISA were transferred from 96-well to 24-well plates. Those cultures which still retained activity were expanded and frozen in liquid nitrogen. The culture with the highest percentage of inhibition was cloned by limiting dilution at 1 cell/well for two clonings (Goding, J. W., Monoclonal Antibodies: Principles and Practice (1983)). The cells were suspended in and fed with 20% (vol/vol) macrophage conditioned medium (Sugasawara, R. J., Cahoon, B. E. and Karu, A. E. J. Immunol. Methods. 79, 263 (1985)). Stabilized cell lines were obtained following the two clonings. The cell line which secreted the most sensitive antibody was identified using CI-ELISA and the antibody specificity was characterized by CI-ELISA and CD-ELISA with respect to aflatoxin metabolites. The subclass of secreted antibody was identified with a kit according to the manufacturers (Boehringer Mannheim) instructions.

Ascites Fluid Production: Mice were primed intraperitoneally with 0.5 ml of pristane 1 to 2 weeks prior to hybridoma injection (Galfre, G., and Milstein, C., Methods in Enzymology. Vol. 73, p. 1–40 (1981)). Each mouse received $1 \times 10^7$ cells suspended in 0.5 ml 20% FBS-DMEM. Abdominal swelling became evident about 10 days following injection and the fluid was tapped within the next week. Fluid was pooled and purified on the same day. The immunoglobulin fraction was precipitated with 100% saturated ammonium sulfate to a final concentration of 50% (Garvey, J. S, Cremer, N. E. and Sussdorf, D. H., Methods in Immunology. 3rd Ed. p. 218–219 (1977)). The pellet was resuspended in PBS, pH 7.2 and dialyzed extensively against 20 mM Tris-HCl, NaCl, pH 8.0. The antibody was lyophilized and stored at $-80°$ C.

RESULTS AND DISCUSSION

Mouse Immunization: To determine if the immunization protocol adequately stimulated plasma cell secretion of aflatoxin $B_1$ specific serum antibody, titers from each of three mice were performed one week following the third antigen injection. Endpoint titers were 1:3200, 1:6400, and 1:6400 for mouse 1, 2, and 3, respectively. To verify if the color development was due to a specific reaction involving anti-aflatoxin $B_1$ antibodies, CI-ELISA was performed. Aflatoxin $B_1$ competed effectively with the solid phase for antibody binding in only the sera from mouse 2 and mouse 3 (Table 1) and the spleen from mouse 2 was used for fusion to the myeloma cells.

Hybridoma Preparation: A double fusion was performed ($2 \times 10^7$ myeloma cells and $2 \times 10^8$ spleen cells) since the spleen from the mouse contained $3 \times 10^8$ cells. The fusion was highly successful and 100% fusion efficiency (number of wells with growing colonies/number of wells seeded) was obtained. All supernatant fractions from 932 wells were screened for desired antibody activity and of these, only 19 showed 40% or more inhibition when the antibody was incubated with 500 ng/ml aflatoxin $B_1$. When antibody activity was further verified in 24-well cultures, following transfer of the 96-well cultures, only 8 were found to retain activity. These cultures, identified as 1B8, 2E7, 2G11, 4C7, 5C11, 7C7, 7G6, and 8B9 were expanded and frozen in liquid nitrogen. Supernatants from fusion wells used to determine antibody sensitivity in CI-ELISA showed that well 4C7, and 2E7 contained cells secreting the most sensitive antibody. Cells from these wells were cloned at 1 cell/well. None of the cells from 2E7 retained activity and only one well from 4C7 contained cells which showed significant inhibition (94% inhibition at 500 ng/ml free aflatoxin $B_1$). This first clone, 4C7-2D6, was recloned at 1 cell/well. Thirty-nine wells contained cells which secreted anti-aflatoxin $B_1$ antibody (63–86% inhibition at 500 ng/ml free aflatoxin $B_1$). Clone 4C7-2D6-2F5 (referred to as 2F5) was shown by CI-ELISA to secrete the most sensitive antibody (86% inhibition at 500 ng/ml free aflatoxin $B_1$).

TABLE 1

Inhibition of serum antibody binding to solid phase following three subcutaneous injections of aflatoxin $B_1$-BSA as determined by a competitive indirect ELISA.

| | Percent Inhibition ng/ml free toxin | | | | |
|---|---|---|---|---|---|
| Mouse No. | 100 | 10 | 1 | 0.1 | 0.1 |
| 1 | 0 | 0 | 0 | 0 | 0 |
| 2 | 44.6 | 44.3 | 28.7 | 33.6 | 23.5 |
| 3 | 28.3 | 16.9 | 10.0 | 8.0 | 0.8 |

Monoclonal Antibody Characterization: The subclass of 4C7-2D6 -2F5 was identified as $IgG_1$ with kappa light chains. The subclass was different than the other monoclonal antibodies previously made to aflatoxin $B_1$. Candlish et al (Candlish, A. A. G., Stimson, W. H. and Smith, J. E., Letters in Appl. Microbiol. 1, 57 (1985)) identified the subclass of 4E1 as $IgG_{2a}$ with kappa light chains. The monoclonal antibody produced by Groopman et al (Groopman, J. D., Trudel, L. J., Donahue, P. R., Marshak-Rothstein, A. and Wogan, G. N., Proc. Natl. Acad. Sci. U.S.A. 81, 7728 (1984)) was an IgM. The difference in the antibody subclasses is not surprising, because the mice were immunized with conjugate antigens prepared differently than the aflatoxin $B_1$-BSA conjugate described herein. The route of immunization and doses were different as well.

Figure 1:
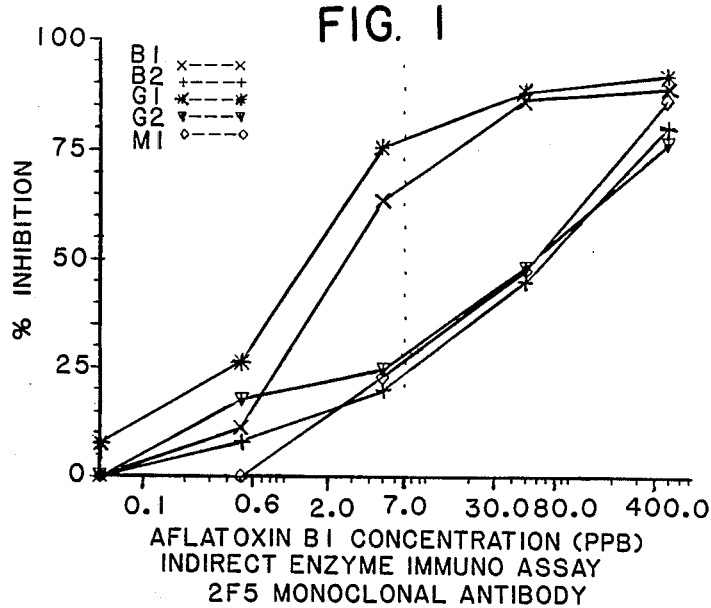

Sensitivity and specificity of the antibody were determined at the same time in a CI-ELISA. The limit of detection was determined to be 0.5 ng/ml or 25 pg/assay (FIG. 1). Using concentrations of aflatoxin $B_1$ and metabolites required to inhibit 50% of the binding of the monoclonal antibody in the CI-ELISA (FIG. 1) as a basis for comparison, the relative cross-reactivities for aflatoxins $B_1$, $B_2$, $G_1$, $G_2$, and $M_1$ were determined (Table 2).

TABLE 2

Comparison of Cross-reactivities among various anti-aflatoxin $B_1$ antibodies towards aflatoxin $B_1$ metabolites.

| | % Cross-reactivity[a] | | | | | |
|---|---|---|---|---|---|---|
| Metabolite | 1[b] (2F5) | 2[c] (2F5) | 3[d] (1C6) | 4[e] | 5[f] | Rabbit[g] |
| Aflatoxin $B_1$ | 100.0 | 100.0 | 100.00 | 100.0 | 100.0 | 100.0 |
| Aflatoxin $B_2$ | 4.0 | 0.2 | 6.7 | 12.6 | 100.0 | 131.6 |
| Aflatoxin $G_1$ | 175.0 | 26.6 | 193.0 | 14.3 | 5.0 | 31.2 |
| Aflatoxin $G_2$ | 5.0 | <0.01 | 2.3 | 1.2 | 3.6 | 1.3 |

TABLE 2-continued

Comparison of Cross-reactivities among various anti-aflatoxin $B_1$ antibodies towards aflatoxin $B_1$ metabolites.

| Metabolite | % Cross-reactivity[a] | | | | | |
|---|---|---|---|---|---|---|
| | $1^b$ (2F5) | $2^c$ (2F5) | $3^d$ (1C6) | $4^e$ | $5^f$ | Rabbit[g] |
| Aflatoxin $M_1$ | 4.5 | 3.7 | 3.9 | 7.3 | 100.0 | 0 |

1,2,3,4 (indirect and direct ELISAs and RIA using monoclonal antibodies)
[a]% cross-reactivity =
$$\frac{\text{Aflatoxin B}_1 \text{ concentration required for 50\% inhibition}}{\text{Metabolite concentration required for 50\% inhibition}} \times 100$$
[b]Described in this example (indirect ELISA)
[c]Described in this example (direct ELISA)
[d]Described in this example (direct ELISA)
[e]Candlish et al, Letters in Appl. Microbiol. 1, 57 (1985) (direct ELISA using monoclonal antibody)
[f]Groopman et al, Proc. Natl. Acad. Sci. USA 81, 7728 (1984) (RIA using monoclonal antibody)
[g]Pestka et al, Appl. Environ. Microbiol. 40, 1027 (1980) (direct ELISA using polyclonal antibody)

The antibody apparently reacted better with aflatoxin $G_1$ than with $B_1$, and to a much lesser extent with aflatoxins $G_2$, $B_2$, and $M_1$. These results suggest that the difuran moiety of aflatoxin was critical to the specificity of antibody raised against the aflatoxin $B_1$-oxime-BSA conjugate. Modifications in the difurans, such as the addition of a hydroxyl in aflatoxin $M_1$ (FIG. 2) decreased the binding significantly. The lack of the double bond in aflatoxins $B_2$ and $G_2$ also lead to a decrease in the ability of the antibody to bind to these metabolites. The cyclopentenone ring did not play a significant role in determining specificity since the modification of this struture to a lactone moiety (B to G series) did not lead to a decreased binding ability of the antibody. Aflatoxin $G_2$ was not found to be highly reactive, while $G_1$ was recognized more readily than aflatoxin $B_1$. The difference in the antibody's ability to bind to the G metabolites must then be reflected in the differences in the difuran rings.

Figure 3:
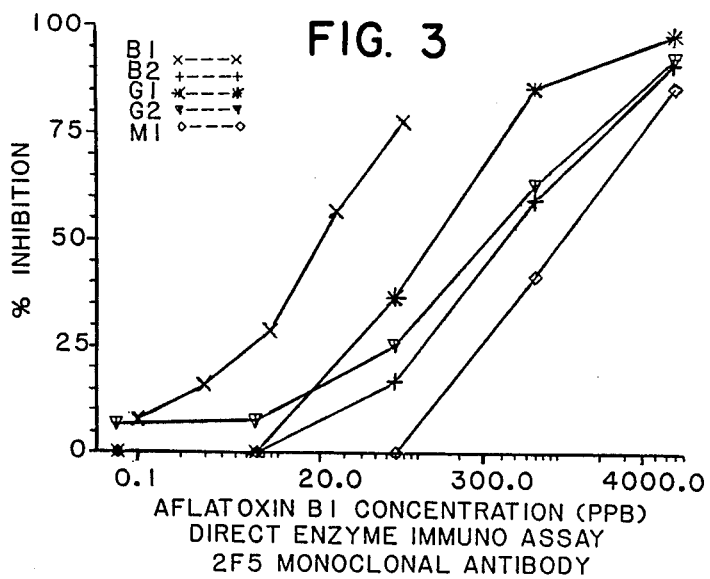
FIG. 3 is a graph similar to FIG. 1, but is a competitive direct-ELISA.

The specificity was also determined by CD-ELISA as shown in FIG. 3 so that a comparison could be made with the specificity of another monoclonal antibdy which was verified using a direct ELISA (Candlish, A. A. G., Stimson, W. H. and Smith, J. E. Letters in Appl. Microbiol. 1, 57 (1985)).

The pattern of cross-reactivity of 4C7-2D6-2F5 was very different than the one determined by RIA for the monoclonal antibody prepared following immunization of mice with a 2,3 epoxide derivative of aflatoxin $B_1$ covalently bound to bovine gamma globulin (Groopman, J. D., Trudel, L. J, Donahue, P. R., Marshak-Rothstein, A. and Wogan, G. N., Proc. Natl. Acad. Sci. U.S.A. 81, 7728 (1984)) (Table 2). The Groopman et al results suggest that the cyclopentenone ring played the key role in determining the specificity since the toxin was conjugated to the carrier protein on the left side of the molecule (difurans), so that the right side would be exposed for recognition. It appeared that the addition of a hydroxyl on the $M_1$ was not recognized, since the antibody bound equally well to aflatoxins $M_1$, $B_2$ and $B_1$. The lactone ring on the right side significantly decreased the antibody's ability to bind to aflatoxins $G_1$ and $G_2$.

All of the monoclonal antibodies displayed about the same degree of sensitivity in the CD-ELISA when compared to each other and when compared with polyclonal systems. The endpoint of detection of 4E1 was 0.2 ng/ml (Candlish, A. A. G., Stimson, W. H. and Smith, J. E., Letters in Appl. Microbiol. 1, 57 (1985)), while the endpoint of detection for the monoclonal antibody prepared by Groopman et al (Groopman, J. D. Trudel, L. J., Donahue, P. R, Marshak-Rothstein, A. and Wogan, G. N., Proc. Natl. Acad. Sci. U.S.A. 81, 7728 (1984)) was determined by RIA to be 300 fmol (0.1 mg/ml).

Preparation of Conjugate Antigens: As previously indicated aflatoxin was conjugated to BSA (aflatoxin $B_1$-BSA) for use as immunogen and to OA (aflatoxin $B_1$-OA) for use as a solid phase antigen in the competitive indirect ELISA (CI-ELISA). Since aflatoxin possesses no reactive groups for conjugation, it was first converted by reaction with carboxymethyloxylamine to aflatoxin $B_1$-N-carboxymethyloxime (aflatoxin $B_1$-oxime by the method of Chu, F. S. and Ueno, I., Appl. Environ. Microbiol. 33, 1125 (1977); and then conjugated to BSA or OA (fraction VII) by the N-hydroxysuccinimide procedure of Kitagawa et al., Chem. Pharm. Bull. 29(4)1130–1135 (1981) The cross linking or conjugating agent can be any well known compound used for this purpose. Preferably carboxymethyloxylamine is reacted with the 1-ketone group of the aflatoxin $B_1$ to form the oxime which is reacted with N-hydroxysuccinimide. The N-hydroxy succinimidyl ester is then reacted with free amino groups on the immunizing protein or enzyme.

Hybridoma-based immunoassays offer simple alternatives for the routine screening of low molecular weight chemical contaminants in agricultural materials. Monoclonal antibodies have been produced against benzo(a)-pyrene (Wallin, H., et al., Cancer Letters, 22, 163–170 (1984)) and various steroids (Eshhar, Z., et al., Steroids 38, 89–109 (1979); Fantl, V., J. Steroid Biochem. 11, 125–130 (1982); Kohen, F., et al., Steroids, 39, 453–459 (1982)) Monoclonal antibodies have recently been produced to several mycotoxins, only some of which actually exhibited improved sensitivity and specificity in immunoassays when compared to polyclonal sera (Gendloff, E. H., et al., Phytopathology (1980); Hunter, K. W., et al., Appl. Environ. Microbiol. 49, 168–172 (1983); Woychik, N. A., et al., Appl. Environ. Microbiol. 48, 1096–1099 (1984)). The present invention is the first description of a monoclonal antibody to aflatoxin $B_1$ and $G_1$ selectivity, which are potential hazards to animal and human health. The 4C7-2D6-2F5 (IVI 10108) hybridoma line offers a continuing supply of antibody with high sensitivity and specificity for aflatoxin $B_1$ and $G_1$ that is readily applicable to the analysis of extracts of cereal grains and feed using CI-ELISA (Liu, M-T., et al., Appl. Environ. Microbiol. 50, 332–336 (1985)) or the competitive direct ELISA (Warner, R., et al., J. Agr. Food Chem. 34:714 (1986)).

The following is the procedure for the storage and for the thawing of the hybridomas.

Procedure for Freezing and Thawing Hybridomas

Thawing of the Cells: The cryovial was removed from the liquid nitrogen. The culture was thawed as quickly as possible. The bottom of the cryovial was immersed in a 37° C. water bath and agitated until the contents were just barely thawed. The exterior of the vial was wiped with 70% EtOH and the contents placed in a 15 ml conical cube previously cooled on ice. Cold 20% FBS-DMEM (10 ml) was added dropwise over a period of about two minutes. The cells were centrifuged at 450×g for eight minutes at 4° C. The centrifugation can be performed at room temperature if a refrigerated centrifuge is not available. The supernatant was removed and the pellet resuspended in 5 ml of 20% FBS-DMEM. The suspension can be placed in a 25 cm² tissue culture flask, or preferably, it should be added to a 24 well plate divided into four aliquots (1.25 ml). The plate was incubated at 37° C. in an atmosphere of 8% $CO_2$. The culture was fed as necessary and transferred from the plate to a small T-flask. The culture was maintained at $1 \times 10^5$ cell/ml.

Freezing of the Cells: All materials were cooled on ice during the procedure. The appropriate volume of culture containing $1 \times 10^6$ cells was placed in a 15-ml conical tube and centrifuged at $450 \times g$ for eight minutes at room temperature. The supernatant was removed and the pellet was resuspended in 0.5 ml of freezing medium. The cryovial was placed in a rack or can which was placed in a styrofoam box and cooled in a $-80°$ C. freezer. Twenty-four hours later the culture was transferred to liquid nitrogen.

Media

1. Dulbecco's Modified eagle's medium (DMEM): DMEM was reconstituted according to the instructions supplied by Gibco, Grand Island, N.Y. Supplements were added to make complete DMEM (10 mM sodium pyruvate, 1% NCTC, 5 mM oxaloacetate, and insulin (75.5 mg/L)).

2. 20% FBS-DMEM: Prepared by adding 20 ml of fetal bovine serum (FBS) and 1 ml of penicillin/streptomycin solution (100.0 U/ml) to 80 ml of complete DMEM. Filter sterilized and stored at 4° C.

3. Freezing Medium: Mixed 10 ml of dimethyl sulfoxide (DMSO) and 90 ml of FBS. Filter sterilized and stored at $-20°$ C.

Assays

Table 3 shows a comparison of the values found for 1C6 and 2F5 and for thin layer chromatography for aflatoxin $B_1$ in naturally contaminated samples of cottonseed, and corn. TLC analyses were made following the AOAC Official Methods of Analysis No. 26.026–26.031. Black light (UV) is used to visualize the aflatoxins on the TLC plate. EIA analyses were made in the direct competitive EIA described in the proceeding disclosure after extracting the samples with 55% methanol (5 parts Methanol to 1 part sample), and defatting the filtered methanol extract with hexane (40% of the original 55% methanol volume).

TABLE 3

Comparison of TLC and EIA for analysis of Aflatoxin $B_1$ in naturally contaminated corn, feed, and cottonseed samples.

| Sample Number | TLC Value | Aflatoxin $B_1$ Monoclonal Antibody | |
|---|---|---|---|
| | | 1C6 | 2F5 |
| CS 18[1] | 8 | 14 | 3 |
| CS 11 | 16 | 12 | 10.5 |
| CS 10 | 30 | 15 | 20 |
| CS 4-3 | 4 | 6 | 8.8 |
| CS 747 | 0 | 5.6 | 0 |
| CS 1 | 40 | 50 | 27 |
| CS 6 | 60 | 50 | 27 |
| CS 592 | 22 | 5.7 | 140 |
| CS 5-19 | 14 | 9.4 | 0 |
| CS 19 | 12 | 13.5 | 0 |
| CS 2 | 18 | 25 | 17 |
| CS 644 | 70 | 35 | 21 |
| CS 7 | 18 | 12.5 | 11.5 |
| CS 3 | 24 | 24.5 | 17 |
| BF 696[2] | 0 | 6.6 | 0 |
| BF 700 | 0 | 2.9 | 5.2 |
| BF 727 | 0 | 6.8 | 7 |
| BF 695 | 0 | 4.5 | 0 |
| BF 135 | 0 | 3.9 | 7 |
| BF 142 | 0 | 5.2 | 0 |
| BF 194 | 240 | 120 | 19 |
| BF 694 | 0 | 2.8 | 0 |
| BF 423 | 9 | 6.4 | 0 |
| BF 426 | 12 | | 11.5 |
| BF 425 | 9 | | 3 |
| BF 699 | 0 | 3.9 | 0 |
| BF 156 | 0 | 4.1 | 15 |
| BF 697 | 0 | 5.6 | 165 |
| BF 999 | 0 | 5.6 | 35 |
| SN 1098 | 0 | 2.5 | |
| SN 6 | 35 | 16 | |

[1] AOAC Method 26.026
[2] AOAC Method 26.052
CS = Cottonseed
BF = Corn or mixed feed
SN = Corn
GL = Corn
SM = Corn Obvious variations will occur to those skilled in the art since the art of preparing hybridomas, monoclonal antibodies and the use thereof in test kits is well developed in the patent arts and literature. It is intended that the present invention be limited only by the hereinafter appended claims.

We claim:

1. A monoclonal antibody produced by a hybridoma resulting from having injected a mouse with a 1-position polypeptide conjugate of aflatoxin $B_1$ and having formed the hybridoma from a myeloma and spleen cells of the mouse, wherein the monoclonal antibody has a specific cross-reactivity for aflatoxins $B_1$ and $G_1$ and limited cross-reactivity to the related aflatoxins $B_2$, $G_2$ and $M_1$ which is the same as specific monoclonal antibody derived from hybridoma IVI-10108.

2. A monoclonal antibody having an aflatoxin $B_1$ reactivity and limited cross-reactivity with aflatoxins $B_2$, $G_2$ and $M_1$ produced by a hybridoma identified as IVI-10108.

3. A hybridoma IVI-10108 producing an antibody having an aflatoxin $B_1$ and $G_1$ cross-reactivity and limited cross-reactivity with aflatoxins $B_2$, $G_2$ and $M_1$.

4. In a test kit for detecting an aflatoxin $B_1$ and $G_1$ as antigens using an immunoassay, the improvement which comprises:

providing in the test kit in a separate container a monoclonal antibody to the aflatoxins $B_1$ and $G_1$, wherein the antibody is derived by repeatedly introducing aflatoxin $B_1$ as a 1-position polypeptide conjugate into a murine so that polyclonal antibodies are provided in the blood serum of the murine, by forming a hybridoma with spleen cells from the murine and myeloma cells and by isolating the hybridoma which produces a monoclonal antibody which specifically binds the aflatoxins $B_1$ and $G_1$, and wherein the monoclonal antibody has a cross-reactivity to aflatoxins $B_2$, $G_2$ and $M_1$ which is the same as a specific monoclonal antibody derived from hybridoma IVI-10108 so that aflatoxins $B_1$ and $G_1$ can be detected.

5. In a test kit for an enzyme immunoassay to determine the presence of unknown antigens aflatoxin $B_1$ and $G_1$ by competitive reaction wherein in the test a known antigen polypeptide or an antibody as a polypeptide are bound to a solid phase, wherein an enzyme is conjugated to the antigen and wherein the enzyme is reacted with a substrate to determine the presence of the unknown antigen, the improvement which comprises:

(a) the solid phase which binds to a known aflatoxin $B_1$ as a polypeptide as the antigen polypeptide or a monoclonal antibody to aflatoxins $B_1$ and $G_1$;

(b) an enzyme conjugate with the aflatoxin $B_1$ wherein the test kit includes a known aflatoxin $B_1$ compound as a standard and wherein the monoclonal antibody is derived from a hybridoma and specifically binds the aflatoxins $B_1$ and $G_1$ and has limited cross-reactivity to aflatoxins $B_2$, $G_2$ and $M_1$ which is the same as a specific monoclonal antibody produced by hybridoma IVI 10108 so that the aflatoxins $B_1$ and $G_1$ can be determined; and (c) a substrate which reacts with the enzyme to determine the unknown antigens aflatoxin $B_1$ and $G_1$ wherein the enzyme conjugate from aflatoxin $B_1$ and substrate are in separate containers.

6. The test kit of claim 5 herein the substrate is 2,2'-azino-di(3-ethylbenzlthiazoline sulfonic acid) which reacts with an initiator peroxide catalyzed by the enzyme to produce a reaction product from the substrate having an optical density of 405 nm which varies as a function of the amount of enzyme as the enzyme conjugate which reacts with the peroxide.

7. In a method for testing for an unknown amount of aflatoxins $B_1$ and $G_1$ in an immunoassay wherein labeled known antigen is used to determine an unknown antigen the improvement which comprises:

(a) providing a monoclonal antibody to the aflatoxins $B_1$ and $G_1$, wherein the monoclonal antibody is derived by repeatedly introducing aflatoxin $B_1$ as a 1-position polypeptide conjugate into a murine so that polyclonal antibodies are provided in the blood serum of the murine, by forming a hybridoma with spleen cells from the murine and myeloma cells and by isolating the hybridoma which produces the monoclonal antibody which is specific for the aflatoxins $B_1$ and $G_1$ and wherein the monoclonal antibody has the same cross-reactivity to related analog compounds $B_2$, $G_2$ and $M_1$ as a specific monoclonal antibody derived from hybridoma IVI-10108; and (b) testing for the unknown amount of aflatoxins $B_1$ and $G_1$ using the monclonal antibody.

* * * * *